United States Patent [19]

Ecanow et al.

[11] Patent Number: 4,596,788

[45] Date of Patent: Jun. 24, 1986

[54] GELATIN AND LECITHIN BASED SYNTHETIC WHOLE BLOOD AND A METHOD OF MAKING THE SAME

[75] Inventors: Charles S. Ecanow, Skokie; Bernard Ecanow, Wilmette, both of Ill.

[73] Assignee: Neomed, Inc., Wilmette, Ill.

[21] Appl. No.: 617,959

[22] Filed: Jun. 7, 1984

Related U.S. Application Data

[60] Division of Ser. No. 464,704, Feb. 7, 1983, Pat. No. 4,539,204, and a continuation-in-part of Ser. No. 437,823, Oct. 29, 1982, abandoned, which is a continuation-in-part of Ser. No. 336,061, Dec. 31, 1981, abandoned, which is a continuation-in-part of Ser. No. 222,364, Jan. 5, 1981, Pat. No. 4,343,797, which is a continuation-in-part of Ser. No. 146,029, May 2, 1980, abandoned, which is a continuation-in-part of Ser. No. 47,021, Jun. 11, 1979, abandoned.

[51] Int. Cl.$^4$ .................. A61K 37/02; A61K 31/685
[52] U.S. Cl. ........................................... 514/2; 514/78
[58] Field of Search ..................................... 514/78, 2

[56] References Cited

U.S. PATENT DOCUMENTS

| | | | |
|---|---|---|---|
| 3,169,094 | 2/1965 | Wretlind | 514/78 |
| 4,001,401 | 4/1977 | Bonsen et al. | 424/177 |
| 4,002,739 | 1/1977 | Turner et al. | 424/177 |
| 4,252,793 | 2/1981 | Altman | 514/78 |

FOREIGN PATENT DOCUMENTS

| | | |
|---|---|---|
| 2940184 | 4/1981 | Fed. Rep. of Germany . |
| 742594 | 12/1955 | United Kingdom . |

OTHER PUBLICATIONS

Watanabe et al.–Chemical Abstracts, vol. 81, (1974), p. 16715v.

A. Veis & C. Aranyi, "Phase Separation in Polyelectrolyte Systems. I. Complex Coacervates of Gelatin", Journal of Physical Chemistry, vol. 64, (1960) pp. 1203–1210.

G. Hawley, Ed., *The Condensed Chemical Dictionary*, 9th Ed., (New York: Van Nostrand Reinhold, 1977), p. 213.

A. Osol, Ed., *Remington's Pharmaceutical Sciences*, (Easton, PA: Mack Publishing Co., 1975), p. 315.

J. McMullen et al, "Pectin–Gelatin Complex Coacervates", *Journal of Pharmaceutical Sciences*, vol. 71, No. 6 (Jun. 1982), pp. 628–633.

R. A. Kahn et al., "Alternative Sources and Substitutes for Therapeutic Blood Components", *Blood*, The Journal of the American Society of Hemotology, vol. 66-1 (Jul. 1985, pp. 1–12.

*Blood Policy & Technology*, Jan. 1985, Office of Technology Assessment, pp. 136–150.

A. Osol, ed., *Remington's Pharmaceutical Sciences, 15th ed.:* (Easton, PA: Mack Publishing Co., 1975), pp. 240–241.

Primary Examiner—Sam Rosen
Attorney, Agent, or Firm—Ladas & Parry

[57] ABSTRACT

A composition of matter which comprises a synthetic whole blood useful as a replacement for whole mammalian blood and a method of making the same are disclosed. The method of manufacture makes use of two gelatins, two modified fluid gelatins, or one gelatin and one modified fluid gelatin of differing isoelectric points, and selected additives. The invention also contemplates the use of only one gelatin or only one modified fluid gelatin, plus lecithin. The invention also contemplates using stroma free hemoglobin, micro-encapsulated stroma free hemoglobin, or synthetic liposomes containing stroma free hemoglobin incorporated in either the coacervate phase or the coacervate system of this invention. The method yields a two phase liquid aqueous system which successfully duplicates the two phase heterogeneous physico-chemical system of naturally occurring whole blood. The disclosed composition possesses many of the physiological capabilities of whole human blood.

25 Claims, No Drawings

GELATIN AND LECITHIN BASED SYNTHETIC WHOLE BLOOD AND A METHOD OF MAKING THE SAME

This application is a division of application Ser. No. 464,704, filed Feb. 7, 1983, now U.S. Pat. No. 4,539,204, and a continuation-in-part of Ser. No. 437,823 filed Oct. 29, 1982, now abandoned, which is a continuation-in-part of Ser. No. 336,061 filed Dec. 31, 1981, now abandoned, which is a continuation-in-part of Ser. No. 222,364 filed Jan. 5, 1981, now U.S. Pat. No. 4,343,797, which is a continuation-in-part of Ser. No. 146,029 filed May 2, 1980, now abandoned, which is a continuation-in-part of Ser. No. 47,021 filed June 11, 1979, now abandoned.

The present invention relates to a synthetic whole blood useful as a replacement for whole mammalian blood and a method of making the same. It has now been unexpectedly discovered that a synthetic blood may be made by incorporating either synthetic liposomes containing stroma free hemoglobin, or microencapsulated hemoglobin into the coacervate phase of an appropriate coacervate system or into an appropriate coacervate system. It has also now been unexpectedly discovered that as long as lecithin is present, a synthetic whole blood may be made using only one gelatin or only one modified fluid gelatin, instead of two.

BACKGROUND OF THE INVENTION

It is now recognized that the physical chemical structure of whole human blood has been successfully duplicated in a composition of matter known as Synthetic Whole Blood, as disclosed in Applicant' U.S. Pat. No. 4,343,797. It is now also recognized that Synthetic Whole Blood is a distinct entity, fundamentally different from the preparations referred to in the scientific literature as "blood substitutes".

An appropriate two-phase aqueous liquid system (i.e. coacervate system) is fundamental to preparation of synthetic whole blood and its companion product, synthetic hematocrit. U.S. Pat. No. 4,343,797 contains the comment, "In the practice of this invention the underlying principle is that any molecule or combination of molecules capable of forming a non-toxic, two-phase, aqueous liquid system can be . . . used to prepare the requisite coacervate system." Further study of the discovery of this principle by the inventors makes it possible to specify this principle in greater detail. The present disclosure further exemplifies this principle.

One category of coacervate systems useful to prepare synthetic whole blood contains among its principal components, (1) a suitable protein, i.e. albumin, gelatin, modified fluid gelatin, etc.; (2) a coacervating surface active molecule such as lecithin; each of these components possessing opposing surface charges; and (3) hemoglobin in the form of synthetic liposomes containing stroma free hemoglobin or stroma free hemoglobin per se, or microencapsulated hemoglobin.

The fundamental components of another category of coacervate systems useful to prepare synthetic whole blood contains (1) two similar or two different protein molecules, i.e. gelatin, modified fluid gelatin, etc., each with a surface charge that opposes the surface charge of the other; and (2) stroma free hemoglobin, microencapsulated hemoglobin or synthetic liposomes containing stroma free hemoglobin.

Appropriate physiologically useful additives can be readily introduced into the compositions derived from either class of the coacervate systems described above.

A number of considerations warrant the development of an alternative version of the Synthetic Whole Blood preparation, as disclosed in U.S. Pat. No. 4,343,797. Principal among these is the probability that a small but medically significant number of persons may be sensitive to one or more of the ingredients of the composition referred to above.

DISCUSSION OF PRIOR ART

Aside from the U.S. Pat. No. 4,343,797, the prior art that has been diligently searched fails to reveal any reference to a preparation which can serve as a whole blood replacement. The literature, however, does contain more than 1500 citations to entities described as "blood substitutes". These citations refer to studies of such substances as perfluorocarbons, albumin, hydroethyl starch, modified gelatin, etc. (References: Chemical Abstracts; 1970–1982; Index Medicus; 1970–1982).

With the single exception of the references to the gelatin preparations used as "blood substitutes", none of the prior art in the clinical literature appears to have any relevance to the presently claimed invention. No citation was identified which hints at, suggests or implies that a synthetic whole blood can be based on gelatin.

To summarize findings from the clinical prior art, from a physiological point of view, regarding available gelatin "blood substitutes", the molecular structure of gelatin is such that in clinical use, it can only serve as a plasma extender, (expand blood volume). It cannot transport any of the physiological gases. (Reference: Merck Index 1979). Unexpectedly, however, through their research applicants have discovered that gelatin and/or modified gelatin based coacervate systems can transport essential amino acids, transport physiologically important gases and restore or maintain the necessary osmotic pressure. There are however additional striking differences. Table I infra of this application lists 13 clinically important variables which distinguish the claimed compositions from the known gelatin "blood substitutes", and which show the similarities between the claimed compositions and whole human blood.

In the prior art, is a reference to gelatin based coacervates, Veis, A. and Aranyi, C., Phase Separation in Polyelectrolyte Systems, I; Complex Coacervates of Gelatin; *Journal of Physical Chemistry*, Volume 64, pages 1203–1205. Examination of this prior art indicates it to be a theoretical study of gelatin based coacervate systems. It addresses only the conditions under which gelatins of differing isoelectric points will form coacervates. There is no suggestion nor inference in this prior art that the described coacervate systems have any possible biological or non-biological use. Therefore, the person ordinarily skilled in the art cannot conclude from a study of this prior art that a synthetic whole blood can be based upon it. Given that gelatin solutions are known to be among the available "blood substitutes", it is more probable that this cited prior art would suggest another method of preparing the already known gelatin based plasma extender.

THE PRESENT INVENTION

The presently disclosed invention rests upon the applicant' recognition of the biological utility of a coacervate system.

However, this recognition is not of itself sufficient to prepare an optimal synthetic whole blood, ready to be administered to mammals, particularly humans. Specific chemical entities, some of which do not of themselves suggest that they are useful in the preparation of a synthetic whole blood, must be added to the coacervate system employed in this invention. It is the applicant' position that these additives alter the chemical character and the physiological utility of the coacervate system, resulting in not another version of a gelatin based "blood substitute" but rather in a synthetic whole blood, which can be used as a replacement for whole mammalian blood.

significantly to enhance the oxygen uptake of these claimed compositions.

OBJECTS

It is an object of this invention to provide an acceptable substitute for whole mammalian blood. It is another object to provide a convenient method for preparing an acceptable substitute for whole mammalian blood. Further objects will appear self evident from the disclosure.

TABLE I

| Properties* | Whole Human Blood | U.S. Pat. No. 4,343,797 Synthetic Whole Blood | Synthetic Whole Blood Gelatin-Gelatin | Synthetic Whole Blood Lecithin-Gelatin | Lactate Ringer's Solution | Dextran | Gelatin including modified gelatin | Albumin 5% | Hydroethyl Starch | Perfluorochemicals |
|---|---|---|---|---|---|---|---|---|---|---|
| 1 | Yes | Yes | Yes | Yes | No | No | No | No | No | Yes |
| 2 | Yes | Yes | Yes | Yes | Yes | Yes | Yes | Yes | Yes | Yes |
| 3 | Yes | Yes | Yes | Yes | No | No | No | No | No | No |
| 4 | Yes | Yes | Yes | Yes | No | No | No | No | No | No |
| 5 | Yes | Yes | Yes | Yes | No | No | No | No | No | Yes |
| 6 | Yes, but not equal to that of synthetic whole blood | Yes | Yes | Yes | No | No | No | No | No | No |
| 7 | No | Yes | Yes | Yes | No | No | No | No | No | No |
| 8 | Yes | Yes | Yes | Yes | No | No | No | No | No | No |
| 9 | Increase | Can be prepared to decrease or increase % | Can be prepared to decrease or increase % | Can be prepared to decrease or increase % | Reduction | Reduction | Reduction | Reduction | Reduction | Reduction |
| 10 | Yes | Yes | Yes | Yes | Yes | Yes | Yes | Yes | Yes | Yes |
| 11 | Yes | No | No | No | Does Not apply | Does Not apply | Does Not apply | Does Not apply | Does Not apply | Yes |
| 12 | No | Yes | Yes | Yes | No | No | No | No | No | Yes |
| 13 | No | Yes | Yes | Yes | Yes | Yes | Yes | Yes | Yes | Yes |

Properties*
1 Oxygen Transport
2 Carbon Dioxide Transfer
3 Oxygen can be held in reserve and released in accordance with physiological tension
4 Hemoglobin can be added or dispersed within the preparation without loss of stability
5 Transfers gasses other than $O_2$ and $CO_2$
6 Possesses both polar and non-polar properties
7 Dissolves and transports non-polar drug entities without loss of dosage-form stability
8 Transports enzyme systems without loss of stability
9 Effect on hematocrit percent after transfusion
10 Essential amino acids can be transported in stable form and desired quantity
11 Oxygen uptake ability reduced at low $O_2$ partial pressures
12 Transports physiologically useful lipid soluble entities as a stable solution
13 Universal donor characteristics As it now appears frequently in the literature, the term synthetic liposomes generically covers both stroma free hemoglobin and other stroma free hemoglobin preparations as well as synthetic erythrocytes or lipid encapsulated hemoglobin. (Reference: Miller, I. and Djordjevich, L.; U.S. Pat. No. 4,133,874 (1979). With regard to the Miller and Djordjevich reference, the possibility is mentioned that the synthetic erythrocytes they have invented can be suspended in isotonic saline or Krebs-Ringer solution or in synthetic plasma materials and used for blood transfusion purposes. Since the vehicles given above contain large quantities of bulk water, there is a strong likelihood that oxygen uptake in such compositions is limited. This stands in direct contrast with the oxygen uptake capability of the presently disclosed invention in which microencapsulated hemoglobin or liposomes containing stroma free hemoglobin is incorporated in the claimed coacervate system or the coacervate phase of such a system. Both the coacervate system and the coacervate phase of the system have significant oxygen pick up. The addition of stroma free hemoglobin in the form given immediately above serves

STATEMENT OF THE INVENTION

Therefore, the present invention provides for a synthetic whole blood comprising two gelatins, two modified fluid gelatins, or one gelatin and one modified fluid gelatin, having different isoelectric points, water, and sufficient alkaline substance to achieve a basic pH, said synthetic whole blood being a substantially non-polar coacervate phase.

It also provides for a synthetic whole blood comprising two gelatins, two modified fluid gelatins, or one gelatin and one modified fluid gelatin, having different isoelectric points, water, and sufficient alkaline substance to achieve a basic pH, said synthetic whole blood being a two-phase system, said phases being a substantially non-polar coacervate phase and a substantially polar equilibrium water phase.

It also provides for a method to make a synthetic whole blood said method comprising (a) combining water and two gelatins two modified fluid gelatins or one gelatin and one modified fluid gelatin with different isoelectric points, (b) storing the combination at 15°–40° C., for 12–72 hours, whereby said combination separates into two layers, said lower layer being a substantially non-polar coacervate phase and said upper layer being a substantially polar equilibrium water phase, (c) separating said lower phase from said upper phase, and (d) adjusting the pH of said lower phase to the range of 7.2–7.6.

It also provides for a method to make a synthetic whole blood, said method comprising (a) combining water and two gelatins, two modified fluid gelatins, or one gelatin and one modified fluid gelatin with different isoelectric points, (b) storing the combination at 15°–40° C., for 12–72 hours, whereby said combination separates into two layers, said lower layer being a substantially non-polar coacervate phase and said upper layer being a substantially polar equilibrium water phase, (c) separating said lower phase from said upper phase, (d) adjusting the pH of said lower phase to the range of 7.2–7.6 and (e) combining said lower coacervate phase of step (c) with said previously separated upper equilibrium water phase.

It also provides for a synthetic whole blood comprising lecithin and either one gelatin or one modified fluid gelatin, water, sufficient alkaline substance to achieve a basic pH, and sufficient electrolyte to achieve an isotonicity equal to that of physiological saline solution, said synthetic whole blood being a substantially non-polar coacervate phase.

It also provides for a synthetic whole blood comprising lecithin and either one gelatin or one modified fluid gelatin, water, sufficient alkaline substance to achieve a basic pH, and sufficient electrolyte to achieve an isotonicity equal to that of physiological saline solution, said synthetic whole blood being a two-phase system, said phases being a substantially non-polar coacervate phase and a substantially polar equilibrium water phase.

It also provides for a method to make a synthetic whole blood, said method comprising (a) combining water and lecithin and either one gelatin or one modified fluid gelatin, (b) mixing in sufficient electrolyte to achieve an isotonicity equal to that of physiological saline solution, and (c) storing the combination at 15°–50° C., for 12–72 hours whereby said combination separates into two layers, said lower layer being a substantially non-polar coacervate phase, and said upper layer being an equilibrium water phase, (d) separating said lower phase from said upper phase and (e) adjusting the pH of said lower phase to the range of 7.2–7.6.

It also provides for a method to make a synthetic whole blood, said method comprising (a) combining water and lecithin and either one gelatin or modified fluid gelatin, (b) mixing in sufficient electrolyte to achieve an isotonicity equal to that of physiological saline solution, and (c) storing the combination at 15°–50° C., for 12–72 hours, whereby said combination separates into two layers, said lower layer being a substantially non-polar coacervate phase, and said upper layer being a substantially polar equilibrium water phase, (d) separating said lower phase from said upper phase, (e) adjusting the pH of said lower phase to the range of 7.2–7.6 and (f) combining said lower coacervate phase of step (d) with said previously separated upper equilibrium water phase.

DETAILED DESCRIPTION OF THE INVENTION

This invention comprises a composition of matter useful as a substitute for whole natural blood. The claimed invention is comprised of a two-phase aqueous liquid system substantially identical to the physicochemical system of whole natural blood. A substantially non-polar coacervate phase insoluble in and in equilibrium with an associated substantially polar equilibrium water phase are characteristic of both naturally occurring whole blood and the claimed invention. This invention also comprises a method of making a whole blood substitute, which yields the two-phase system referred to above. The system is composed of an internal suspension phase, herein referred to as the coacervate phase, and an external suspension phase which is the associated equilibrium water phase. When the claimed composition is introduced intravenously, it will disperse in the blood plasma of the recipient, and thereby contribute to the two-phase physicochemical system of the naturally occurring whole blood. The physiochemical characteristics of this invention render it sensitive to and reactive to the oxygen tension of the recipient's blood. Further, it can readily enter and pass through the major blood vessels, capillaries and the microcirculation system.

The claimed synthetic whole blood can transport and transfer oxygen and carbon dioxide much as naturally occurring erythrocytes do, without adversely affecting the percent of the recipient's hematocrit. In addition, it can carry nutrients, physiological entities, therapeutic drugs and enzyme systems.

Upon transfusion this invention can establish, re-establish and/or maintain normal osmotic pressures. The transport characteristics of this composition of matter enable it to serve as a safe and reliable vehicle. When it is desirable to introduce enzyme systems into the body, such systems as noted above can be added to this invention and infused through conventional intravenous methods. Enzyme systems introduced through these compositions of matter will perform their normal physiological functions.

The guidelines which determine the quantities of the claimed synthetic whole blood which may be safely infused are substantially identical to those which govern the use of whole blood.

By reason of its mode of manufacture and its physicochemical structure, the claimed whole blood substitute posseses a number of advantages over whole blood. Thus, prior to infusion this invention can be modified to meet many of the specific requirements of given treatment procedures, such as hyperalimentation, intravenous drug therapy, open heart surgery, etc. By way of example, additional quantities of stroma free hemoglobin or synthetic liposomes containing stroma free hemoglobin or microencapsulated hemoglobin can be incorporated in a given embodiment of this invention so as to enable more oxygen to be carried for longer periods of time as would be desirable in treatment of certain blood diseases or in instances of prolonged surgery. Electrolytes can be added to the claimed substance for use in the treatment of cases of severe burns or shock resulting from the loss of blood. In embodiments containing added electrolytes, adjustments to isotonicity are made following such additions. When nutrients must be quickly introduced and/or when the circulatory system is the preferred route for nutrition, essential amino acids and other nutritional agents can be added prior to transfusion.

A significant advantage of this invention is that because this invention possesses universal donor characteristics, no blood typing is necessary prior to administration of this composition.

Other important advantages of this invention may be enumerated as follows: the components of the claimed composition are abundant, readily available and relatively inexpensive. Additives can be quickly introduced to previously prepared, stored embodiments. The invention can be used without the need for highly specialized equipment or technology. The constituents of the claimed composition of matter and the method of preparing it eliminates the problems associated with the storage of whole blood.

PREFERRED METHOD

In order to more fully explain the invention, the following is a general description of the preferred method used to practice this invention. Specific examples of the practice of this invention are also provided in the following section of this disclosure.

The formulation that follows specifies substantially equal proportions of two gelatins, two modified fluid gelatins, or one gelatin and one modified fluid gelatin, with different isoelectric points. However, in the practice of this invention unequal proportions of the two gelatins, two modified fluid gelatins, or one gelatin and one modified fluid gelatin with different isoelectric points may also be used to prepare the claimed composition of matter.

In the process of manufacture, the component ingredients should be prepared and combined under aseptic conditions.

Mix equal proportions of a 1 to 10% weight to volume solution of gelatin with an isoelectric point of 2 to 6 with a 1 to 10% weight to volume solution of gelatin, an isoelectric point of 8.0 to 10.0. In this step, modified fluid gelatins may be used in place of gelatin provided the requirement of differing isoelectric points is observed. The resultant mixture of the two gelatin solutions will be approximately 0.5 to 5% weight to volume of each of said gelatins. The mixture is then left undisturbed at 37 degrees C. for 24 hours. At the end of this period, the mixture will have separated into two layers, the lower one of which comprises the coacervate phase. The upper layer comprises the equilibrium water phase and may be discarded. The pH of the coacervate phase is adjusted to 7.4 by the addition, preferably dropwise, of any nontoxic alkaline substance, preferably sodium hydroxide or sodium bicarbonate. The resulting composition can be used as a synthetic whole blood. In the preferred procedure, 2 to 15% weight to volume of stroma free hemoglobin, or that amount of synthetic liposomes containing stroma free hemoglobin or microencapsulated hemoglobin as will result in a 2 to 15% weight to volume of stroma free hemoglobin in the finished product, is added to augment the oxygen transport capability of the composition. If desired, 1 to 10% weight to volume of a nontoxic ionic, or non-ionic surfactant and/or a nontoxic organic solvent may be added to the preparation, to enhance the oxygen transport capability of the composition. A suitable protein such as albumin may also be added. In such instance it is added in the amount of 1 to 5% weight volume.

The non-ionic surfactants that may be used, include any of the nontoxic pluronics or any of the substances known as spans.

The ionic surfactants that may be used include any of the phospholipids such as lecithin, cephalin, isolecithin, sphingomyelin, phosphatidyl serine, phosphatidic acid, phosphatidyl inositol and phosphatidyl choline. Other compounds known to those skilled in the art may also be used. Lecithin is the preferred phospholipid in this invention and is added in the amount of 1 to 10% weight to volume.

Following the addition of any of the above, or any combination of the above, the preparation is subjected to vigorous shaking for three minutes to achieve uniform dissolution and dispersion of the additive(s). It is highly desired that for the best method that when the ingredients referred to above are added, the amounts of each should be sufficient to reach the saturation point and beyond within the coacervate phase.

If the intended use of the composition involves an open circuit, prior to infusion, oxygen should be bubbled through the preparation until the desired oxygen concentration is reached. If the synthetic whole blood composition is to be used in a closed system, the desired level of oxygen tension is maintained by bubbling oxygen through the system by the usual means.

Another variation of this invention also useful as a whole blood substitute is also claimed. This variation makes use of both layers. The preferred manufacturing procedure is as follows: The claimed two phase liquid aqueous system is prepared in the manner described previously. After the 24 hour period of storage at 37 degrees C. the two layers are separated by means of a separatory funnel or other suitable means but, the equilibrium water layer is retained in sterile condition for use in a subsequent manufacturing step. Following the separation procedure, the pH of the coacervate layer is adjusted to 7.25 to 7.4 by the dropwise addition of sodium hydroxide or sodium bicarbonate. When this step is completed, 2 to 15% weight to volume of stroma free hemoglobin, or that amount of synthetic liposomes containing stroma free hemoglobin or microencapsulated hemoglobin is added so that the stroma free hemoglobin in the finished product ranges from 2 to 15% weight to volume, is added and the preparation vigorously mixed. The preparation is then emulsified by adding the previously separated equilibrium water layer and using a colloid mill or other suitable means to produce the required emulsion. The particles of the emulsion can range in size from 0.5 to 9 microns in size. In the preferred procedure, the addition of the equilibrium water layer and the emulsifying step follow the addition and mixing of 2 to 15% weight to volume of stroma free hemoglobin, or synthetic liposomes containing stroma free hemoglobin or microencapsulated hemoglobin. Also, 1 to 10% of a suitable ionic surfactant, preferably lecithin, and 1 to 5% weight to volume of a suitable protein, preferably albumin, may be added.

When preparation of the composition is completed, it may be infused to transport physiological gases, restore or maintain osmotic pressure, transport polar and nonpolar drugs, carry enzyme systems, nutriments, etc. Alternatively, it can be stored at from 4 to 10 degrees C. until needed. If the composition is to be infused into a human following refrigerated storage it should be warmed to body temperature (37 degrees C.).

It may be stored at conventional room temperatures, if the preparation can be maintained in completely sterile condition.

While the above description contains many specifics these should not be construed as limitations on the scope of the invention but rather as exemplifications of preferred embodiments. Accordingly, the scope of this invention should not be determined by the described embodiments but by the appended claims and their legal equivalents.

SPECIFIC EXAMPLES

Examples of how the claimed compositions of matter may be prepared follow.

Sterile conditions are observed during all phases of manufacture.

EXAMPLE 1

Take 4 grams of gelatin, isoelectric point of 9 and add distilled water until a solution of 100 mls is reached. Next, take 4 grams of gelatin, isoelectric point of 4, and add distilled water until a solution of 100 mls is reached. Mix the two solutions thoroughly and incubate, undisturbed at 37 degrees C. for 24 hours. Separate the resulting two layers and discard the upper equilibrium water layer. Adjust the pH of the lower (coacervate) layer to 7.4 through the dropwise addition of sodium hydroxide, and add 10% weight to volume of stroma free hemoglobin. Disperse the additive by vigorous shaking for 4 minutes. If the preparation is to be infused shortly after manufacture, bubble oxygen through the composition until desired oxygen level is reached.

EXAMPLE 2

The procedure follows that of Example 1 except that 5% weight to volume of lecithin is also added to the coacervate layer, and dispersed by shaking the mixture.

EXAMPLE 3

The procedures follows that of Example 1 except that 2% weight to volume of albumin is also added to the coacervate layer and dispersed by vigorously shaking the mixture.

EXAMPLE 4

The procedure follows that of Example 1 except that 5% weight to volume of stroma free hemoglobin, 5% weight to volume of lecithin, and 1% weight to volume of albumin are added to the coacervate layer and dispersed by means of vigorous shaking the composition.

EXAMPLE 5

Mix equal proportions of 8% weight to volume of gelatin with an isoelectric point of 5, and a gelatin with an isoelectric point, of 9.5. Let the mixture stand undisturbed for 24 hours at 37 degrees C. At the end of this period, separate the two layers that will have formed and discard the upper layer. Adjust the pH of the lower layer to 7.4 by the dropwise addition of sodium hydroxide. To this, add 5% weight to volume of stroma free hemoglobin. Disperse the stroma free hemoglobin by vigorous shaking of the composition.

EXAMPLE 6

The procedure follows that of Example 5 except that 5% weight to volume of lecithin is added to the coacervate layer and dispersed by vigorous shaking of the composition.

EXAMPLE 7

The procedures follows that of Example 6 except that 1% weight to volume of albumin is added to the coacervate layer and dispersed by vigorous shaking of the composition.

EXAMPLE 8

Thoroughly mix equal proportions of 8% weight to volume of modified liquid gelatin with an isoelectric point of 5, and a modified liquid gelatin with an isoelectric point of 9. Permit the mixture to stand undisturbed at 37 degrees C. for 24 hours. At the end of this period, separate the two layers that will have formed and discard the upper layer. Adjust the pH of the lower layer to 7.4 by the dropwise addition of sodium hydroxide. Add 10% weight to volume of stroma free hemoglobin and disperse same by vigorous shaking for 4 minutes.

EXAMPLE 9

The procedure follows that of Example 8 except that 5% weight to volume of lecithin is added to the coacervate layer and dispersed through vigorous shaking of the composition.

EXAMPLE 10

The procedure follows that of Example 8 except that 1% weight to volume of albumin is added to the coacervate layer and dispersed through vigorous shaking of the mixture.

EXAMPLE 11

The procedure follows that of Example 8 except that 5% weight to volume of lecithin and 1% weight to volume of albumin are added to the coacervate layer and dispersed through vigorous shaking of the composition.

EXAMPLE 12

This is the procedure employing encapsulated stroma free hemoglobin. It occurs after the coacervate system has been formed, the phases are separated, and 2 to 5% stroma free hemoglobin has been added to the lower coacervate layer. This procedure thus may be applied to the resultant product of any of Examples 4, 5, 6, 7, 8, 9, 10 and 11. The lower coacervate layer containing the stroma free hemoglobin is combined with the equilibrium liquid water layer and emulsified so that the final emulsion contains particles (droplets) which can range from 0.5 to 9 microns in size. Next, 1 to 5% formaldehyde solution is added dropwise to the emulsified preparation until the desired degree of shell structuring of the droplets is achieved. The degree of structuring can range from semi-solid or gel-like to rigid, and is achieved either through the amount of formaldehyde added or through the length of the period of storage. After the desired degree of structuring is achieved, the preparation is stored anywhere between 5 to 40 hours at 20° to 40° C. On removal from storage, the preparation will have separated into two layers, the bottom one of which contains microencapsulated globules substantially spherical in shape, containing stroma free hemoglobin. The upper layer consists of equilibrium liquid water. The two layers are separated by means of a separatory funnel or other acceptable means. The microencapsulated spheres are washed with the equilibrium liquid water, until substantially all traces of formaldehyde are completely removed. The microencapsulated spheres containing stroma free hemoglobin can then be dispersed in physiological saline solution, in the coacervate phase of any of the herein described coacervate systems, or added to the coacervate phase of the two phase coacervate system. After this step, the composition is then emulsified. The resultant emulsion is prepared so that the droplets can range in size from 0.5 to 9 microns. When the microencapsulated spheres containing stroma free hemoglobin are incorporated into the two phase coacervate system as described above, the result of the procedure is microencapsulated globules containing stroma free hemoglobin incorporated in droplets of the coacervate phase which in turn is suspended in the equilibrium liquid water phase.

In practice, where optimal sustained oxygen uptake and release is desired, minimal structuring of the microencapsulated spheres is preferred. Depending upon the physiological effect to be achieved, differing proportions of microencapsulated spheres of differing degrees of shell hardness can be combined. This will result in special release effects which can be used when introducing drugs, nutrients, enzyme systems. In other words, the composition can be so prepared as to give the desired specific rate of release of any of the components contained within the microencapsulated spheres. The procedure to incorporate drugs, nutrients, enzyme systems, et cetera, into synthetic blood containing microencapsulated stroma free hemoglobin is the same as the procedure herein described to incorporate drugs, nutrients, enzyme systems, et cetera, into synthetic blood containing microencapsulated hemoglobin.

EXAMPLE 13

Take 4 grams of gelatin, isoelectric point of 9 and add distilled water until a solution of 100 mls is reached. Next, take 4 grams of gelatin, isoelectric point of 4, and add distilled water until a solution of 100 mls is reached. Mix the two solutions thoroughly and incubate, undisturbed at 37 degrees C. for 24 hours. Separate the resulting two layers. Adjust the pH of the lower (coacervate) layer to 7.4 through the dropwise addition of sodium hydroxide, add 10% weight to volume of stroma free hemoglobin. Disperse the additive by vigorous shaking.

The preparation is then emulsified by adding the previously separated equilibrium water layer and using a colloid mill to produce the emulsion. The desired emulsion particle size can range from 0.54 to 9 microns in size.

EXAMPLE 14

The procedure follows that of Example 12 except that 5% weight to volume of lecithin is also added to the coacervate layer.

EXAMPLE 15

The procedure follows that of Example 12 except that 2% weight to volume of albumin is also added to the coacervate layer.

EXAMPLE 16

The procedure follows that of Example 12 except that 5% weight to volume of stroma free hemoglobin, 5% weight to volume lecithin and 1% weight to volume albumin are added to the coacervate layer.

EXAMPLE 17

Mix equal proportions of 8% weight of volume of modified gelatin, isoelectric point of 5 and with a second modified gelatin, isoelectric point of 9.5, incubate 24 hours at 37 degrees C. At the end of this period, separate the two layers that will have formed. Adjust the pH of the lower coacervate layer to 7.4 by the dropwise addition of sodium hydroxide. Add 5% weight to the volume of stroma free hemoglobin. Disperse the stroma free hemoglobin by vigorous shaking.

The previously separated equilibrium water layer is then added to the preparation and a colloid mill is used to produce the emulsion. The desired emulsion particle size can range from 0.5 to 9 microns.

EXAMPLE 18

The procedure follows that of Example 16 except that 5% weight to volume of lecithin is added to the coacervate layer.

EXAMPLE 19

The procedure follows that of Example 16 except that 1% weight to volume of albumin is also added to the coacervate layer.

EXAMPLE 20

The procedure follows that of Example 16 except that 5% weight to volume of stroma free hemoglobin, 5% weight to volume of stroma free hemoglobin, 5% weight to volume lecithin and 1% weight to volume albumin are added to the coacervate layer.

EXAMPLE 21

The procedure follows that of Example 16 except that (a) 8% weight to volume of modified fluid gelatin, isoelectric point of 5 is mixed with an equal amount of gelatin isoelectric point of 9 and (b) instead of stroma free hemoglobin being dispersed, synthetic liposomes containing stroma free hemoglobin are dispersed by vigorous mixing into the formed coacervate system.

EXAMPLE 22

Mix equal proportions of 8% weight to volume of gelatin with an isoelectric point of 5, and a gelatin with an isoelectric point, of 9.5. Let the mixture stand undisturbed for 24 hours at 37 degrees C. At the end of this period, separate the two layers that will have formed and discard the upper layer. Adjust the pH of the lower layer to 7.4 by the dropwise addition of sodium hydroxide. To this, add 5% weight to volume of synthetic liposomes containing stroma free hemoglobin. Disperse the synthetic liposomes containing stroma free hemoglobin by vigorously mixing the composition.

EXAMPLE 23

Thoroughly mix equal proportions of 8% weight to volume of modified liquid gelatin with an isoelectric point of 5, and a modified liquid gelatin with an isoelectric point of 9. Permit the mixture to stand undisturbed at 37 degrees C. for 24 hours. At the end of this period, separate the two layers that will have formed and discard the upper layer. Adjust the pH of the lower layer to 7.4 by the dropwise addition of sodium hydroxide. Add 10% weight to volume of synthetic liposomes containing stroma free hemoglobin and disperse same by vigorous shaking for 4 minutes.

EXAMPLE 24

Mix 5 to 10% weight to volume of gelatin, isoelectric point 7 to 10, with ½ to 10% weight to volume of lecithin. Adjust the electrolyte concentration to give an isotonicity equal to that of physiological saline solution. Incubate at 37° C. for 24 hours, at the end of which 2 layers will have separated, one of which is the equilibrium water phase and the other is the coacervate phase. Separate the resulting two layers and discard the upper equilibrium water layer. Adjust the pH of the lower (coacervate) layer to 7.4 through the dropwise addition of sodium hydroxide. Add 10% weight to volume of stroma free hemoglobin. Disperse the additive by vigorous shaking for 4 minutes. If the preparation is to be infused shortly after manufacture, bubble oxygen through the composition until the desired oxygen level is reached.

EXAMPLE 25

Mix ½ to 10% weight to volume of gelatin or modified fluid gelatin, isoelectric point of 5 to 10, with ½ to 10% weight to volume of lecithin. Add by mixing in such amounts of a salt of sodium, potassium, calcium and magnesium as will result in the electrolyte balance and isotonicity of physiological saline solution. Incubate at 37° to 50° C. for 24 to 36 hours. At the end of the period of incubation, the mixture will have separated into two layers, the bottom one of which is known as the coacervate phase. The upper layer is known as the equilibrium water phase. At this point the two phases may be separated by means of a separatory funnel. Stroma free hemoglobin or liposomes containing stroma free hemoglobin or microencapsulated hemoglobin is added to the coacervate phase in an amount that will result in a finished product that contains 2 to 15% weight to volume of stroma free hemoglobin. The preparation described immediately above can be used for transfusion or stored at from 4° to 10° C. Alternatively, the coacervate phase which contains the electrolytes and stroma free hemoglobin or liposomes containing stroma free hemoglobin or microencapsulated stroma free hemoglobin in the quantities given above can be combined with the equilibrium water phase and emulsified. The emulsion can be used for transfusion or stored at 4° to 10° C.

EXAMPLE 26

The amounts used were as follows: 5% weight to volume gelatin, isoelectric point of 7, and 7% weight to volume of lecithin. All other ingredients were in the amounts given above, for Example 24, and the procedure followed the description given above. The two phases were emulsified as described above. Stroma free hemoglobin was used, in the amount of 5% weight to volume.

EXAMPLE 27

This procedure is the same as Example 24 except that the phases were separated and no emulsification was used, i.e. the coacervate phase plus the described additives constituted the composition.

EXAMPLE 28

This procedure is the same as Example 24 except that modified fluid gelatin was used.

EXAMPLE 29

The procedure is the same as Example 24 except that modified fluid gelatin was used.

EXPERIMENT

The following in vitro experiment was conducted to test the oxygen carrying capacity of the claimed composition. Control substances were comprised of (A) saline solution, and (B) saline solution and 4% weight to volume stroma free hemoglobin. The three compositions according to this invention were comprised of (C) gelatin based coacervate composition of this invention, (D) gelatin based coacervate composition of this invention plus 4% weight to volume of stroma free hemoglobin, and (E) emulsified gelatin based coacervate composition of this invention plus 4% weight to volume of stroma free hemoglobin.

Oxygen was bubbled through each for 20 minutes at 37° C. The results obtained were as follows:

| Substance | | Oxygen uptake (Volume to volume) |
|---|---|---|
| (A) | Saline solution | 0% |
| (B) | Saline solution and 4% hemoglobin | 1% |
| (C) | Claimed composition (Gelatin P.I.3; Gelatin P.I.9)* | 10% |
| (D) | Claimed composition and 4% stroma free hemoglobin (Gelatin P.I.3; Gelatin P.I.9)* | 22% |
| (E) | Emulsified claimed composition containing 4% hemoglobin | 15% |
| (F) | Claimed composition: Coacervate Phase (Lecithin and Gelatin, P.I.9) | 12% |
| (G) | Claimed Composition: Coacervate Phase (Lecithin, Gelatin P.I.9; 4% stroma free hemoglobin) | 19% |
| (H) | Claimed composition: emulsified (Lecithin, Gelatin P.I.9 and 4% stroma free hemoglobin) | 14% |

*P.I. is an abbreviation for isoelectric point.

We claim:

1. A synthetic whole blood substitute comprising effective amounts of lecithin and either one gelatin or one modified fluid gelatin, water, sufficient alkaline substance to achieve a pH within the range of human blood, and sufficient electrolyte to achieve an isotonicity equal to that of physiological saline solution, said synthetic whole blood comprising essentially a substantially non-polar coacervate phase of an aqueous two-phase coacervate system.

2. The synthetic whole blood substitute of claim 1, wherein said gelatin or modified fluid gelatin has an isoelectric point of from about 2 to 10; said pH is from about 7.2 to 7.6; said alkaline substances is sodium hydroxide or sodium bicarbonate; said lecithin is present as a starting material in an amount of about 0.5–10% weight to volume of water; said gelatin or modified fluid gelatin is present as starting material in an amount of about 1–10% weight to volume of water; and said electrolyte is a salt of Na, K, Ca, or Mg.

3. The synthetic whole blood substitute of claim 2, wherein said synthetic whole blood also includes about 2–25% weight to volume stroma free heloglobin, about 1–10% weight to volume of an ionic surfactant or a non-ionic surfactant or mixtures of the surfactants, about 1–10% weight to volume of an organic solvent, about 1–5% weight to volume of a suitable protein, or mixtures thereof.

4. The synthetic whole blood substitute of any of claims 1, 2, or 3, further including an additive selected from physiological entities.

5. A synthetic whole blood substitute comprising effective amounts of lecithin and either one gelatin or one modified fluid gelatin, water, sufficient alkaline substance to achieve a pH within the range of human blood, and sufficient electrolyte to achieve an isotonicity equal to that of physiological saline solution, said synthetic whole blood comprising a two-phase system, including a substantially non-polar coacervate phase and a substantially polar equilibrium water phase.

6. The synthetic whole blood substitute of claim 5, wherein said gelatin or modified fluid gelatin has an isoelectric point of from about 2 to 10; said pH is from about 7.2 to 7.6; said alkaline substance is sodium hydroxide or sodium bicarbonate; said lecithin is present as a starting material in an amount of about 0.5–10% weight to volume of water; said gelatin or modified fluid gelatin is present as a starting material in an amount of about 1–10% weight to volume of water; said electrolyte is a salt of Na, K, Ca, or Mg; and said blood substitute composition being in the form of an emulsion wherein the particle size is in the range of about 0.5–9 microns.

7. The synthetic whole blood substitute of claim 6, wherein said synthetic whole blood also includes about 2–15% weight to volume stroma free hemoglobin, about 1–10% weight to volume of an ionic surfactant or a non-ionic surfactant or mixtures of the surfactants, about 1–10% weight to volume of an organic solvent, about 1–5% weight to volume of a suitable protein, or mixtures thereof.

8. The synthetic whole blood substitute of any of claims 5, 6, or 7, further including an additive selected from physiological entities.

9. A method of making a synthetic whole blood substitute, said method comprising the steps of: (a) combining water and effective amounts of lecithin and either one gelatin or modified fluid gelatin, (b) mixing in sufficient electrolyte to achieve an isotonicty equal to that of physiological saline solution, (c) storing the combination at a temperature of about 15°–50° C., for about 12–72 hours whereby said combination separates into two layers, the lower layer being a substantially non-polar concervate phase, and the upper layer being a substantially polar equilibrium water phase, (d) separating said lower phase from said upper phase, and (e) adjusting the pH of said lower phase to the range of from about 7.2–7.6.

10. The method of claim 9, wherein in step (a) said gelatin or modified fluid gelatin is combined with water to form a 1–10% weight to volume solution, said lecithin is combined with water to form a 0.5–10% weight to volume solution, and then said two solutions are combined; and said gelatin or modified gelatin has an isoelectric point of 2 to 10, and in step (b) said electrolyte is a salt of Na, K, Ca, or Mg.

11. The method of claim 10, wherein said pH is adjusted to 7.4 by the dropwise addition of an alkaline substance, selected from sodium bicarbonate or sodium hydroxide.

12. The method of claim 11, wherein after said pH adjustment, 1–5% weight to volume of a suitable protein is added.

13. The method of claim 12, wherein after said pH adjustment, 2–15% weight to volume of stroma free hemoglobin is added.

14. The method of claim 12, wherein after said pH adjustment, 1–10% weight to volume of an ionic surfactant or a non-ionic surfactant or mixtures of the surfactants is added.

15. The method of claim 14, wherein after said pH adjustment, 1–10% weight to volume of an organic solvent is added.

16. The method of any of claims 9, 10, 11, 12, 13, 14, or 15, further including the addition of an additive selected from, physiological entities.

17. The method of claim 9, including the additional step of: (f) recombining said non-polar coacervate phase with said previously separated polar equilibrium water phase.

18. The method of claim 17, wherein in step (f), said combining is achieved by emulsification, thereby forming an emulsion.

19. The method of claim 18, wherein the particles of said emulsion range in size from about 0.5–9 microns.

20. The synthetic whole blood substitute of any of claims 1, 2 or 3, further including an additive selected from nutrients or therapeutic entities.

21. The synthetic whole blood substitute of any of claims 1, 2, or 3, further including an additive selected from drugs, enzyme systems, electrolytes, $O_2$ or mixtures thereof.

22. The synthetic whole blood substitute of any of claims 5, 6, or 7, further including an additive selected from nutrients or therapeutic entities.

23. The synthetic whole blood substitute of any of claims 5, 6, or 7, further including an additive selected from drugs, enzyme systems, electrolytes, $O_2$ or mixtures thereof.

24. The method of any of claims 9, 10, 11, 12, 13, 14 or 15, further including the addition of an additive selected from nutrients or therapeutic entities.

25. The method of any of claims 9, 10, 11, 12, 13, 14 or 15, further including the addition of an additive selected from drugs, enzyme systems, electrolytes, $O_2$ or mixtures thereof.

* * * * *